United States Patent
Murray et al.

(10) Patent No.: US 6,566,462 B2
(45) Date of Patent: May 20, 2003

(54) MULTIPLE CATALYST SYSTEM

(75) Inventors: Rex E. Murray, Cross Lanes, WV (US); Simon Mawson, Charleston, WV (US); John F. Szul, Nitro, WV (US); Kersten Anne Erickson, South Charleston, WV (US); Tae Hoon Kwack, Belle Mead, NJ (US); Frederick J. Karol, Belle Mead, NJ (US); David James Schreck, Cross Lanes, WV (US)

(73) Assignee: Univation Technologies, LLC, Houston, TX (US)

( * ) Notice: Subject to any disclaimer, the term of this patent is extended or adjusted under 35 U.S.C. 154(b) by 3 days.

(21) Appl. No.: 09/974,193

(22) Filed: Oct. 10, 2001

(65) Prior Publication Data

US 2002/0107341 A1 Aug. 8, 2002

Related U.S. Application Data

(62) Division of application No. 09/455,883, filed on Dec. 6, 1999, now Pat. No. 6,340,730.

(51) Int. Cl.[7] .............................. C08F 4/44; C08F 4/16; B01J 31/38
(52) U.S. Cl. ...................... 526/114; 526/118; 526/160; 526/161; 526/133; 526/943; 502/152; 502/155
(58) Field of Search ................ 526/160, 161, 526/170, 171, 172, 133, 134, 113, 114, 118; 502/152, 155

(56) References Cited

U.S. PATENT DOCUMENTS

| | | | |
|---|---|---|---|
| 4,935,474 A | 6/1990 | Ewen et al. | 526/114 |
| 5,464,905 A | 11/1995 | Tsutsui et al. | 525/240 |
| 5,527,752 A | 6/1996 | Reichle et al. | 502/117 |
| 5,693,727 A | 12/1997 | Goode et al. | 526/86 |
| 6,069,213 A * | 5/2000 | Nemzek et al. | 526/113 |

FOREIGN PATENT DOCUMENTS

| | | | |
|---|---|---|---|
| EP | 0770629 A2 | | 5/1997 |
| EP | 0 889 061 A1 | * | 1/1999 |
| WO | WO98/02247 | | 1/1998 |
| WO | WO99/01460 | | 1/1999 |
| WO | 99 01460 | | 1/1999 |
| WO | WO 99/01460 | * | 1/1999 |
| WO | WO99/03899 | | 1/1999 |

OTHER PUBLICATIONS

Database WPI, Section Ch, Week 199622, Derwent Publications Ltd., London, GB; AN 1996–217262, XP002156624 & JP 08 081515 A (Mitsubishi Chem Corp), Mar. 26, 1996.

* cited by examiner

Primary Examiner—David W. Wu
Assistant Examiner—R. Harlan
(74) Attorney, Agent, or Firm—Jaimes Sher; Lisa Kimes Jones (57) ABSTRACT

This invention relates to a process to polymerize olefins comprising reacting olefins with a catalyst system comprising an activator, a metallocene and a second metal compound based on bidentate ligands containing heterocycle moieties.

18 Claims, 2 Drawing Sheets

MULTIPLE CATALYST SYSTEM

CROSS-REFERENCE TO RELATED APPLICATIONS

The present application is a Divisional of U.S. Application Ser. No. 09/455,883, filed Dec. 6, 1999, now issued as U.S. Pat. No. 6,340,730.

FIELD OF THE INVENTION

This invention relates to the use of two or more different metal compounds, preferably in the same reactor, used to produce polyolefins.

BACKGROUND OF THE INVENTION

Metallocene compounds are of particular interest in the polyolefin industry today for their use as polymerization catalysts. For example both biscyclopentadienyl and monocyclopentadienyl transition metal compounds (particularly of groups 4, 5 and 6) are known to polymerize olefins when used in combination with an activator, such as an alumoxane or a non-coordinating anion. Likewise U.S. Pat. No. 5,527,752 discloses a new class of olefin polymerization catalysts based on complexes of a transition metal having pi bonded ligands and heteroallyl moieties combined with an activator such as an alumoxane or a non-coordinating anion. Further, copending U.S. patent application 09/103,620 filed Jun. 23, 1998 (published as WO 99/01460) assigned to Union Carbide discloses new transition metal compounds based on bidentate ligands containing pyridine or quinoline moieties for use on olefin polymerizations.

These new catalysts, such as the metallocene polymerization catalysts (i.e. those containing a transition metal bound to at least one cyclopentadienyl, indenyl or fluorenyl group), have recently been used to produce new resins having desirable product properties. For example metallocene catalyst systems are used by Exxon Chemical Company to produce EXCEED™ type polyethylene resins. While these resins have excellent toughness properties, particularly dart impact properties, they, like other metallocene catalyzed polyethylenes can be difficult to process on older equipment. One of the means used to improve the processing of metallocene catalyzed polyethylenes is to blend them with high density polyethylene. This, however, is expensive and adds a cumbersome blending step to the manufacturing/fabrication process.

Higher molecular weight confers desirable mechanical properties and stable bubble formation onto polyethylene polymers. However, it also inhibits extrusion processing by increasing backpressure in extruders, promoting melt fracture defects in the inflating bubble and potentially, promotes too high a degree of orientation in the finished film. To remedy this, one may form a secondary, minor component of lower molecular weight polymer to reduce extruder backpressure and inhibit melt fracture. Several industrial processes operate on this principle; using multiple reactor technology.

Another option used to address this processability problem has been to try to produce the two polymers together at the same time in the same reactor using two different catalysts. Mobil in their patent application WO 99/03899, discloses using a metallocene type catalyst and a Ziegler-Natta type catalyst in the same reactor to produce a bimodal molecular weight distribution (Mw/Mn) high density polyethylene. These resins however still do not have a preferred balance of processability and strength properties.

Other dual catalyst systems have been used in the past for a variety of reasons. For example WO 98/02247 discloses a dual catalyst system of a metallocene and a non-metallocene ($TiCl_4$+alcohol) treated with the contact product of dialkylmagnesium and trialkylsilanol. WO 98/02247 discloses dual metallocene systems and describes the idea that the two different transition metal sources exhibit a different hydrogen response under the same polymerization and hydrogen conditions as critical. Hydrogen response is the sensitivity of the catalyst to manipulation by adding or subtracting hydrogen to or from the polymerization system to produce different products. Likewise, U.S. Pat. No. 4,935,474 discloses olefin polymerization in the presence of two or more metallocenes (activated with alumoxane) each having a different propagation and termination rate constants. U.S. Pat. No. 5,464,905 discloses a molding polymer composition which comprises a copolymer blend produced from a copolymer produced from two different metallocenes combined with alumoxane and a second copolymer produced with a metallocene and alumoxane. Liquid mixtures of many classes of catalysts are disclosed for use in gas phase polymerization in U.S. Pat. No. 5,693,727. U.S. Pat. No. '727 discloses that more than one liquid metallocene may be employed. Similarly, EP 0 770 629 A discloses a process to produce bimodal polymers using two reactors in series. In some circumstances only the reaction conditions and monomer feeds are changed in the second reactor. In other circumstances a second different catalyst is added to the second reactor.

Mitsui, for example, and others produce a processable bimodal molecular weight distribution (MWD) high density polyethylene product under the Tradename HIZEX™ which is considered a worldwide standard for this type of HDPE product. HIZEX™ is produced in two or more reactors at a substantial cost. While bimodal MWD HDPE products have these desirable characteristics, they can be inherently costly to produce because they require a series- or cascade-reactor system. In such systems, each reactor in a multiple reactor process produces a single component of the final product. Thus, there is a need in the art to produce a processable polyethylene having a good balance of haze and gloss with improved physical properties in one reactor.

An option used to address this processability problem has been to try to produce two polymers together at the same time in the same reactor using two different catalysts. Mobil in PCT patent application WO 99/03899, discloses using a metallocene type catalyst and a Ziegler-Natta type catalyst in the same reactor to produce a bimodal molecular weight distribution (MWD) high-density polyethylene (HDPE). These resins however still do not have a preferred balance of processability and strength properties. Thus, there is a desire for a processable polyethylene polymers arising from a single reactor process having desirable processing, mechanical and optical properties.

This invention provides a dual catalyst system that can be used in one reactor to produce processable polyethylene.

BRIEF DESCRIPTION OF THE INVENTION

This invention relates to a process to polymerize olefins comprising reacting one or more olefins with a catalyst system comprising at least two metal compounds and an activator in a gas or slurry phase reactor. The first metal compound is preferably a metallocene and the second metal compound is preferably a transition metal compound based on bidentate ligands containing heterocycle moieties. Preferably the metal compounds are selected in such a way that one produces high molecular weight polymer and another produces lower molecular weight polymer.

DETAILED DESCRIPTION OF THE INVENTION

Figure 1:
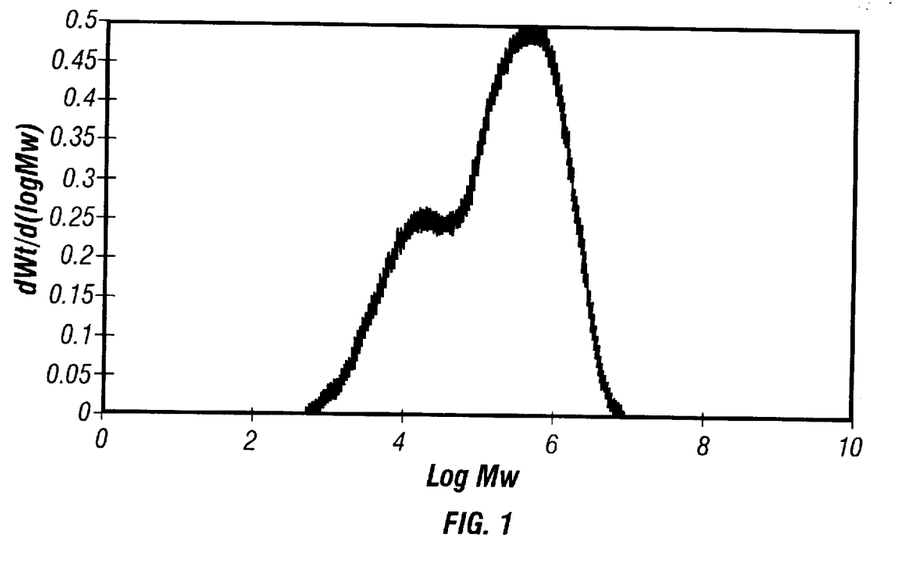
FIG. 1 is the SEC graph for Example 1.
Figure 2:
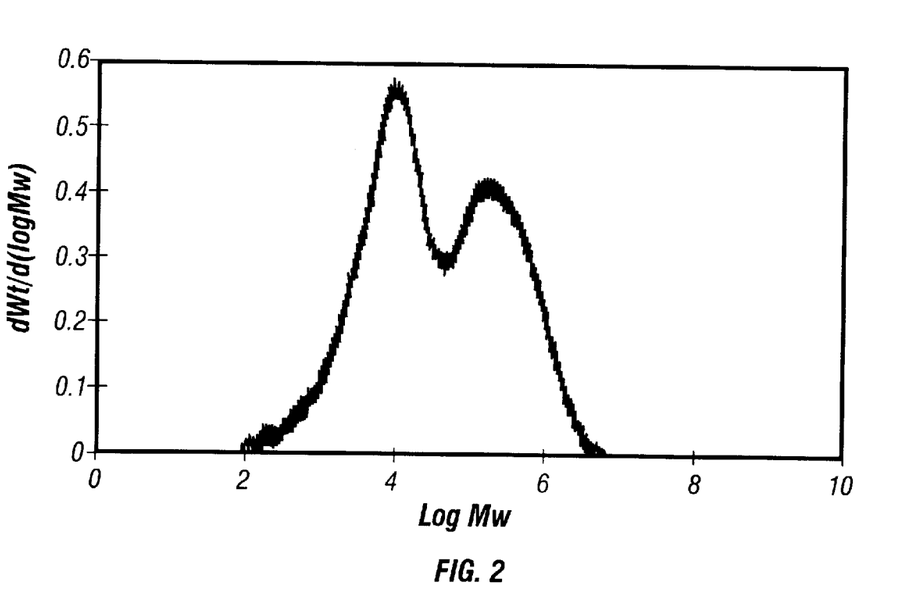
FIG. 2 is the SEC graph for Example 2.
Figure 3:
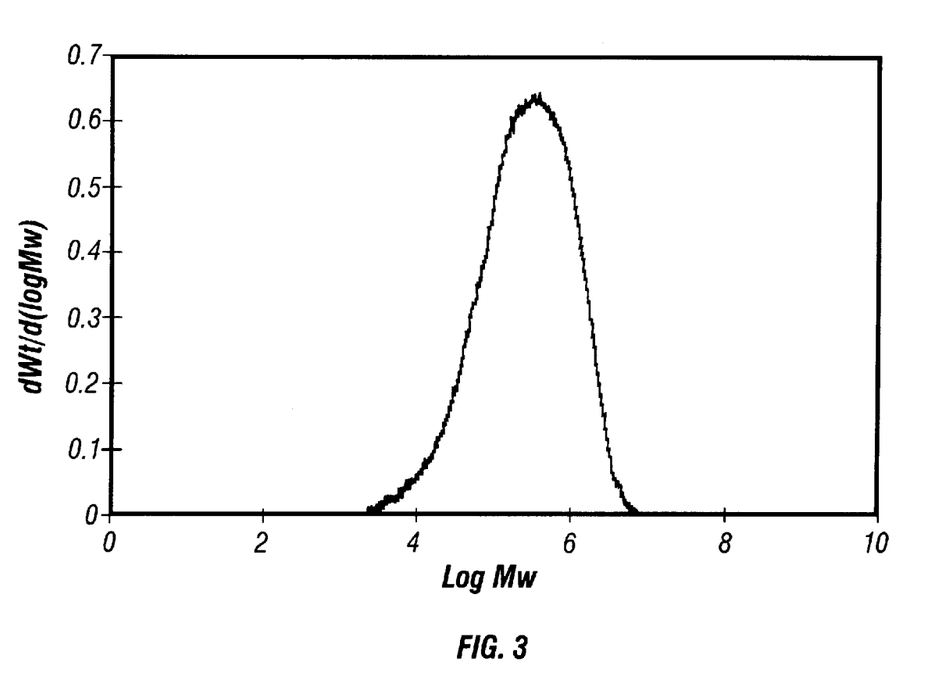
FIG. 3 is the SEC graph for Example 5.

In a preferred embodiment this invention relates to a process to polymerize olefins comprising contacting olefins with a catalyst system comprising at least two metal compounds and at least one activator in a slurry phase or gas phase reactor wherein the first metal compound is a metallocene catalyst (for purposes of this invention metallocene is defined to include those compounds containing a transition metal bound to at least one cyclopentadienyl, indenyl or fluorenyl group or other similar functioning structure, preferably a group 4, 5 or 6 metal bound to a cyclopentadienyl, indenyl or fluorenyl group) and the second metal compound is a transition metal compound based on bidentate ligands containing pyridine or quinoline moieties.

In a preferred embodiment the metallocenes comprise bulky ligand transition metallocene-type catalyst compounds including half and full sandwich compounds having one or more bulky ligands including cyclopentadienyl structures or other similar functioning structure such as pentadiene, cyclooctatetraendiyl and imides. The bulky ligands are capable of η-5 bonding to a transition metal atom, for example from Group 4, 5 and 6 of the Periodic Table of Elements.

Bulky ligand transition metallocene-type catalyst systems of the invention are formed from the bulky ligand metallocene-type catalyst compound represented by the formula:

$$(L^p)_m M(A^q)_n (E')_o \quad (III)$$

where L is a bulky ligand, substituted or unsubstituted; M is a transition metal (preferably a group 4, 5 or 6 transition metal), p is the anionic charge of L and m is the number of L ligands and m is 1, 2 or 3, A is a ligand bonded to M and capable of inserting an olefin between the M—A bond, q is the anionic charge of A and n is the number of A ligands and n is 1, 2, 3 or 4, and E is an anionic leaving group such as but not limited to hydrocarbyl, hydride, halide, carboxylate or combination thereof or any other anionic ligands; r is the anionic charge of E and o is the number of E ligands and o is 1, 2, 3 or 4 such that (p×m)+(q×n)+(r×o) is equal to the formal oxidation state of the metal center; and activated by an activation system. The activator is preferably an aluminum alkyl, alumoxane, modified alumoxane or any other oxy-containing organometallic compound or non-coordinating anion, or a combination thereof.

In another embodiment, when using non-coordinating anions, the bulky ligand transition metallocene-type catalyst systems are preferably those complexes represented by the formula:

$$\{[(L^p)_m M(A^q)_n]^{+k}\}_h [B'^{-j}]_i \quad (IV)$$

where L is a substituted or unsubstituted bulky ligand bonded to M, p is the anionic charge of L and m is the number of L ligands and m is 1, 2 or 3; A is a ligand bonded to M and capable of inserting an olefin between the M—A bond, q is the anionic charge of A and n is the number of A ligands and n is 1, 2, 3 or 4, M is a transition metal, and (p×m)+(q×n)+k corresponds to the formal oxidation state of the metal center; where k is the charge on the cation and k is 1, 2, 3 or 4, and B' is a chemically stable, non-nucleophillic anionic complex, preferably having a molecular diameter of 4 Å or greater and j is the anionic charge on B', h is the number of cations of charge k, and i the number of anions of charge j such that h×k=j×i. Such a system may be added preformed to the polymerization or produced in situ the polymerization.

In formulas (III) and (IV) above, any two L and/or A ligands may be bridged to each other and/or unbridged. The catalyst compound may be full-sandwich compounds having two or more ligands L, which are cyclopentadienyl derived ligands or substituted cyclopentadienyl derived ligands, or half-sandwich compounds having one ligand L, which is a cyclopentadienyl derived ligand or heteroatom substituted cyclopentadienyl derived ligand or hydrocarbyl substituted cyclopentadienyl derived ligand or moiety such as an indenyl ligand, a benzindenyl ligand or a fluorenyl ligand, an octahydrofluorenyl ligand, a cyclooctatetraendiyl ligand, an azenyl ligand and the like, including hydrogenated versions thereof or any other ligand structure capable of η-5 bonding to the transition metal atom. One or more of these bulky ligands is π-bonded to the transition metal atom; each L can be substituted with a combination, which can be the same or different. Non-limiting examples of substituents include hydrogen or linear, branched alkyl radicals or cyclic alkyl, alkenyl, alkynl or aryl radicals or combination thereof having from 1 to 30 carbon atoms or other substituents having up to 50 non-hydrogen atoms that can also be substituted. Non-limiting examples of alkyl substituents include methyl, ethyl, propyl, butyl, pentyl, hexyl, cyclopentyl, cyclohexyl, benzyl or phenyl groups and the like, including all their isomers, for example tertiary butyl, iso propyl etc. Non-hydrogen substituents include the atoms carbon, silicon, nitrogen, oxygen, tin, germanium and the like including olefins. L may also be other types of bulky ligands including but not limited to bulky amides, phosphides, alkoxides, aryloxides, imides, carbolides, borollides, porphyrins, phthalocyanines, corrins and other polyazomacrocycles. The metal atom, from the Periodic Table of the Elements, may be a Group 3 to 10 metal, preferably, a Group 4, 5 or 6 transition metal or a metal from the lanthanide or actinide series, more preferably the transition metal is from Group 4. Other ligands may be bonded to the transition metal, such as a leaving group, such as but not limited to weak bases such as amines, phosphines, ether, carboxylates, dienes, hydrocarbyl radicals having from 1 to 20 carbon atoms or halogens and the like. In addition to the transition metal, these ligands may be optionally bonded to A or L. Non-limiting examples of such catalyst components and catalyst systems are discussed in for example, U.S. Pat. Nos. 4,530,914, 4,871,705, 4,937,299, 5,124,418, 5,017, 714, 5,120,867, 5,210,352, 5,278,264, 5,278,119, 5,304,614, 5,324,800, 5,347,025, 5,350,723, 5,391,790, 5,391,789, 5,399,636, 5,539,124, 5,455,366, 5,534,473, 5,684,098, 5,693,730, 5,698,634, 5,710,297, 5,712,354, 5,714,427, 5,714,555, 5,728,641 and 5,728,839 all of which are herein fully incorporated by reference. Also, the disclosures of European publications EP-A-0 591 756, EP-A-0 520 732, EP-A-0 420 436, EP-B1 0 485 822, EP-B1 0 485 823, EP-A2-0 743 324 and EP-B1 0 518 092 and PCT publications WO 91/04257, WO 92/00333, WO 93/08221, WO 93/08199, WO 94/01471, WO 96/20233, WO 97/15582, WO 97/19959, WO 97/46567, WO 98/01455 and WO 98/06759 are all herein fully incorporated by reference.

In one embodiment of the invention the bulky ligand transition metallocene-type catalyst systems of the invention include monocyclopentadienyl heteroatom containing transition metal metallocene-type compounds. These metallocene-type compounds are activated by an alumoxane, modified alumoxane, a non-coordinating anion, a Lewis acid or a combination thereof to form an active polymerization catalyst system. These types of catalyst systems are described in, for example, PCT publication WO 92/00333, WO 94/07928, WO 91/04257, WO 94/03506, WO 96/00244 and WO 97/15602 and U.S. Pat. Nos. 5,057,475, 5,096,867, 5,055,438, 5,198,401, 5,227,440 and 5,264,405 and European publication EP-A-0 420 436, all of which are herein fully incorporated by reference. Additionally it is within the scope of this invention that the metallocene catalysts and catalyst systems may be those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401 and 5,723,398 and PCT publications WO 93/08221, WO 93/08199 and WO 95/07140 and European publications EP-A-0 578 838, EP-A-0 638 595, EP-B-0 513 380 and EP-A1-0 816 372, all of which are herein fully incorporated by reference.

The preferred transition metal component of the metallocene-type catalyst of the invention are those of Group 4, particularly, titanium, zirconium and hafnium. The transition metal may be in any formal oxidation state, preferably +2, +3 or +4 or a mixture thereof, more preferably +4.

In one embodiment, the metallocene is represented by the formula:

$$(C_5H_{5-d-f}R''_d)_eR'''_fMQ_{g-e} \quad (V)$$

wherein M is a Group 4, 5, 6 transition metal, $(C_5H_{5-d-f}R''_d)$ is the same or different unsubstituted or substituted cyclopentadienyl ligand bonded to M, each R", which can be the same or different, is hydrogen or a substituent group containing up to 50 non-hydrogen atoms or substituted or unsubstituted hydrocarbyl having from 1 to 30 carbon atoms or combinations thereof, or two or more carbon atoms are joined together to form a part of a substituted or unsubstituted ring or ring system having 4 to 30 carbon atoms, R''' is one or more or a combination of carbon, germanium, silicon, tin, phosphorous or nitrogen atoms containing radical bridging two $(C_5H_{5-d-f}R''_d)$ ligands, or bridging one $(C_5H_{5-d-f}R''_d)$ ligand to M; each Q which can be the same or different is a hydride, substituted or unsubstituted hydrocarbyl having from 1 to 30 carbon atoms, halogen, alkoxides, aryloxides, amides, phosphides, or any other univalent anionic ligand or combination thereof; also, two Q's together form an alkylidene ligand or cyclometallated hydrocarbyl ligand or other divalent anionic chelating ligand, where g is an integer corresponding to the formal oxidation state of M, d is 0, 1, 2, 3, 4 or 5, f is 0 or 1 and e is 1, 2 or 3.

In another preferred embodiment of this invention the metallocene is a monocylopentadienyl catalyst component represented by the formula:

wherein M is Ti, Zr or Hf, $(C_5H_{5-y-x}R_x)$ is a cyclopentadienyl ring which is substituted with from 0 to 5 substituent groups R, "x" is 0, 1, 2, 3, 4 or 5 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a heteroatom, such as a halogen atom, $C_1$–$C_{20}$ hydrocarbyl-substituted metalloid radicals wherein the metalloid is selected from the Group 14 of the Periodic Table of Elements, and halogen radicals or $(C_5H_{5-y-x}R_x)$ is a cyclopentadienyl ring in which two adjacent R-groups are joined forming $C_4$–$C_{20}$ ring to give a saturated or unsaturated polycyclic cyclopentadienyl ligand such as indenyl, tetrahydroindenyl, fluorenyl or octahydrofluorenyl;

$(JR'_{z-1-y})$ is a heteroatom ligand in which J is an element with a coordination number of three from Group 15 or an element with a coordination number of two from Group 16 of the Periodic Table of Elements, preferably nitrogen, phosphorus, oxygen or sulfur with nitrogen being preferred, and each R' is, independently a radical selected from a group consisting of $C_1$–$C_{20}$ hydrocarbyl radicals wherein one or more hydrogen atoms is replaced by a halogen atom, y is 0 or 1, and "z" is the coordination number of the element J;

each Q is, independently any univalent anionic ligand such as halogen, hydride, or substituted or unsubstituted $C_1$–$C_{30}$ hydrocarbyl, alkoxide, aryloxide, amide or phosphide, provided that two Q may be an alkylidene, a cyclometallated hydrocarbyl or any other divalent anionic chelating ligand; and n may be 0,1 or 2;

A is a covalent bridging group containing a Group 15 or 14 element such as, but not limited to, a dialkyl, alkylaryl or diaryl silicon or germanium radical, alkyl or aryl phosphine or amine radical, or a hydrocarbyl radical such as methylene, ethylene and the like;

L' is a Lewis base such as diethylether, tetraethylammonium chloride, tetrahydrofuran, dimethylaniline, aniline, trimethylphosphine, n-butylamine, and the like; and w is a number from 0 to 3. Additionally, L' may be bonded to any of R, R' or Q and n is 0, 1, 2 or 3.

It is contemplated in some embodiments, that the bulky ligands of the metallocene-type catalyst compound of the invention described above are asymmetrically substituted in terms of additional substituents or types of substituents, and/or unbalanced in terms of the number of additional substituents on the bulky ligands or the bulky ligands themselves are different. It is also contemplated that in one embodiment, the metallocene-type catalysts of the invention include their structural or optical or enantiomeric isomers and mixtures thereof.

In another preferred embodiment the metallocene is a compound as described in U.S. Pat. Nos. 5,527,752 and 5,747,406 and EP-B1-0 735 057, all of which are herein fully incorporated by reference. Preferably, the metallocene compound is represented by one of the following formulae:

(VII)

(VIII)

wherein M is a transition metal from Group 4, 5 or 6, preferably titanium, zirconium or hafnium, most preferably zirconium or hafnium; L is a substituted or unsubstituted, pi-bonded ligand coordinated to M, preferably L is a cycloalkadienyl bulky ligand, for example cyclopentadienyl, indenyl or fluorenyl bulky ligands, optionally substituted with one or more hydrocarbyl substituent groups having from 1 to 20 carbon atoms; each Q is independently selected from the group consisting of —O—, —NR—, —CR$_2$— and —S—, preferably oxygen; Y is either C or S, preferably carbon; Z is selected from the group consisting of —OR, —NR$_2$, —CR$_3$, —SR, —SiR$_3$, —PR$_2$, —H, and substituted or unsubstituted aryl groups, with the proviso that when Q is —NR— then Z is selected from the group consisting of —OR, —NR$_2$, —SR, —SiR$_3$, —PR$_2$ and —H, preferably Z is selected from the group consisting of —OR, —CR$_3$ and —NR$_2$; n is 1 or 2, preferably 1; A is a univalent anionic group when n is 2 or A is a divalent anionic group when n is 1, preferably A is a carbamate, carboxylate, or other heteroallyl moiety described by the Q, Y and Z combination; and each R is independently a group containing carbon, silicon, nitrogen, oxygen, and/or phosphorus where one or more R groups may be attached to the L substituent, preferably R is a hydrocarbon group containing from 1 to 20 carbon atoms, most preferably an alkyl, cycloalkyl, or an aryl group and one or more may be attached to the L substituent; and T is a bridging group selected from the group consisting of alkylene and arylene groups containing from 1 to 10 carbon atoms optionally substituted with carbon or heteroatom(s), germanium, silicon and alkyl phosphine; and m is 2 to 7, preferably 2 to 6, most preferably 2 or 3.

In the formulas VII and VIII, the supportive substituent formed by Q, Y and Z is a unicharged polydentate ligand exerting electronic effects due to its high polarizability, similar to the cyclopentadienyl ligand. In the most preferred embodiments of this invention, the disubstituted carbamates and the carboxylates are employed. Non-limiting examples of these mono-bulky ligand metallocene-type catalyst compounds include indenyl zirconium tris(diethylcarbamate), indenyl zirconium tris(trimethylacetate), indenyl zirconium tris(p-toluate), indenyl zirconium tris(benzoate), (1-methylindenyl)zirconium tris(trimethylacetate), (2-methylindenyl) zirconium tris(diethylcarbamate), (methylcyclopentadienyl) zirconium tris(trimethylacetate), cyclopentadienyl tris(trimethylacetate), tetrahydroindenyl zirconium tris(trimethylacetate), and (pentamethylcyclopentadienyl) zirconium tris(benzoate). Preferred examples are indenyl zirconium tris(diethylcarbamate), indenyl zirconium tris(trimethylacetate), indenyl zirconium-trispivalate and (methylcyclopentadienyl) zirconium tris(trimethylacetate).

In a preferred embodiment the second metal compound is represented by the formula:

$$((Z)XA_t(YJ))_qMQ_n \qquad (I)$$

where M is a metal selected from Group 3 to 13 or lanthanide and actinide series of the Periodic Table of Elements; Q is bonded to M and each Q is a monovalent, divalent or trivalent anion; X and Y are bonded to M; X and Y are independently carbon or a heteroatom, provided that at least one of X and Y is a heteroatom, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms or a silyl group, an alkyl silyl group such as a trialkyl silyl, preferably Z is a cyclic group containing 3 to 50 atoms, preferably 3 to 30 carbon atoms; t is 0 or 1; when t is 1, A is a bridging group joined to at least one of X, Y or J, preferably X and J; q is 1 or 2; n is the oxidation state of M minus q if Q is a monovalent anion, n is (the oxidation state of M—q)2, if Q is a bivalent anion or n is (the oxidation state of M—q)/3 if Q is a trivalent anion, typically n is an integer from 1 to 4 depending on the oxidation state of M. In one embodiment, if X is oxygen or sulfur then Z is optional. In another embodiment, if X is nitrogen or phosphorous then Z is present. In an embodiment, Z is preferably an aryl group, more preferably a substituted aryl group.

In another embodiment, the second metal compounds are represented by the formula:

$$((R'_mZ)XA(YJR''_p))_qMQ_n \qquad (II)$$

where M is a metal selected from Group 3 to 13 of the Periodic Table of Elements, preferably a Group 4 to 12 transition metal, more preferably a Group 4, 5 or 6 transition metal, even more preferably a Group 4 transition metal such as titanium, zirconium or hafnium, and most preferably zirconium;

Each Q is bonded to M and each Q is a monovalent, divalent or trivalent anion. Preferably each Q is independently selected from the group consisting of halogens, hydrogen, alkyl, aryl, alkenyl, alkylaryl, arylalkyl, hydrocarboxy or phenoxy radicals having 1–20 carbon atoms. Each Q may also be amides, phosphides, sulfides, silylalkyls, diketonates, and carboxylates. Optionally, each Q may contain one or more heteroatoms, more preferably each Q is selected from the group consisting of halides, alkyl radicals and arylalkyl radicals. Most preferably, each Q is selected from the group consisting of arylalkyl radicals such as benzyl.

X and Y are both bound to M and are independently carbon or a heteroatom, provided that at least one of X and Y is a heteroatom, X and Y are preferably each heteroatoms, more preferably X and Y are independently selected from the group consisting of nitrogen, oxygen, sulfur and phosphorous, even more preferably nitrogen or phosphorous, and most preferably nitrogen;

Y is contained in a heterocyclic ring or ring system J. J contains from 2 to 30 carbon atoms, preferably from 2 to 7 carbon atoms, more preferably from 3 to 6 carbon atoms, and most preferably 4 or 5 carbon atoms. Optionally, the heterocyclic ring J containing Y, may contain additional heteroatoms. J may be substituted with R" groups that are independently selected from the group consisting of hydrogen or linear, branched, cyclic, alkyl radicals, or alkenyl, alkynyl, alkoxy, aryl or aryloxy radicals. Also, two or more R" groups may be joined to form a cyclic moiety such as an aliphatic or aromatic ring. Preferably R" is hydrogen or an aryl group, most preferably R" is hydrogen. When R" is an aryl group and Y is nitrogen, a quinoline group is formed. Optionally, an R" may be joined to A;

Z is a hydrocarbyl group bonded to X, preferably Z is a hydrocarbyl group of from 1 to 50 carbon atoms, preferably Z is a cyclic group having from 3 to 30 carbon atoms, preferably Z is a substituted or unsubstituted cyclic group containing from 3 to 30 carbon atoms, optionally including one or more heteroatoms, more preferably Z is an aryl group, most preferably a substituted aryl group in another embodiment Z may be silyl or an alkyl silyl, preferably a trialkyl silyl;

Z may be substituted with R' groups that are independently selected from group consisting of hydrogen or linear, branched, alkyl radicals or cyclic alkyl, alkenyl, alkynyl or aryl radicals. Also, two or more R' groups may be joined to form a cyclic moiety such as an aliphatic or aromatic ring. Preferably R' is an alkyl group having from 1 to 20 carbon atoms, more preferably R' is methyl, ethyl, propyl, butyl, pentyl and the like, including isomers thereof, more preferably R' is a methyl group, or a primary, secondary or tertiary hydrocarbon, including isopropyl, t-butyl and the like, most preferably R' is an isopropyl group. Optionally, an R' group may be joined to A. It is preferred that at least one R' is ortho to X;

A is a bridging group joined to at least one of, preferably both of, X and J. Bridging group A contains one or more Group 13 to 16 elements from Periodic Table of Elements. More preferably A contains one or more Group 14 elements, most preferably A is a substituted carbon group, a di-substituted carbon group or vinyl group; and In formula (II) m and p are independently an integer from 0 to 5, preferably m is 2; n is the oxidation state of M minus q if Q is a monovalent anion, n is (the oxidation state of M—q)/2, if Q is a bivalent anion or n is (the oxidation state of M—q)/3 if Q is a trivalent anion, preferably n is an integer from 1 to 4; and q is 1 or 2, and where q is 2, the two ((R'$_m$Z)XA(YJR"$_m$)) of formula (II) are bridged to each other via a bridging group, preferably a bridging group containing a Group 14 element.

In a preferred embodiment when n is 2 or 3 in formula I or II one Q group is a hydrocarboxy group, a boronate or an amide. In another preferred embodiment when n is 2 or 3 in formula I or II, then one Q group is an alkoxide, phenoxide, acetylacetonate, carboxylate, cyclopentadienyl, flourenyls or an indenyl group.

In one embodiment of the invention, the second metal compound is represented by the formula:

wherein $R_a$ and $R_b$ are each independently selected from the group consisting of alkyl, aryl, heterocyclic groups, and hydrogen; $R_c$ and $R_d$ are each independently selected from the group consisting of alkyl, aryl, and hydrogen; and each L is a monovalent, bivalent, or trivalent anion, preferably independently selected from the group consisting of halogens; hydrogen; alkyl, aryl, alkenyl, alkylaryl, arylalkyl, hydrocarboxy radicals having 1–20 carbon atoms; amides; phosphides; sulfides; silylalkyls; diketonates; and carboxylates. More preferably, each L is selected from the group consisting of halides, alkyl radicals, and arylalkyl radicals. Most preferably, each L is selected from the group consisting of arylalkyl radicals such as benzyl. Each L may contain one or more heteroatoms.

In another embodiment of the invention, the second metal compound is represented by the formula:

wherein $R_a$, $R_b$, $R_c$, $R_d$, and L have the meanings stated above.

In yet another embodiment of the invention, the second metal compound is represented by the formula:

wherein $R_a$, $R_b$, $R_c$, $R_d$, and L have the meanings stated above.

In another preferred embodiment of the invention, the second metal compound is represented by the formula:

Compound 1

In another particularly preferred embodiment of the invention, the second metal compound is represented by the formula:

Compound 2

In a further preferred embodiment of the invention, the second metal compound is represented by the formula:

Compound 3

Yet another preferred second metal compound is represented by the formula:

Compound 4

Ph = phenyl.

In a preferred embodiment the metallocene and the second metal compound are based upon the same metal, preferably a group 4 metal, preferably Zr, Hf or Ti, preferably Zr.

The metal compounds described herein are preferably combined with one or more activators to form an olefin polymerization catalyst system. Preferred activators include alkyl aluminum compounds (such as diethylaluminum chloride), alumoxanes, modified alumoxanes, non-coordinating anions, non-coordinating group 13 metal or metalloid anions, boranes, borates and the like. It is within the scope of this invention to use alumoxane or modified alumoxane as an activator, and/or to also use ionizing activators, neutral or ionic, such as tri (n-butyl) ammonium tetrakis (pentafluorophenyl) boron or a trisperfluorophenyl boron metalloid precursor which ionize the neutral metallocene compound. Other useful compounds include triphenyl boron, triethyl boron, tri-n-butyl ammonium tetraethylborate, triaryl borane and the like. Other useful compounds include aluminate salts as well.

In a preferred embodiment modified alumoxanes are combined with the first and second metal compounds to form a catalyst system. In a preferred embodiment MMAO3A (7.0 wt % Al in heptane, commercially available from Akzo Chemicals, Inc. under the trade name Modified Methylalumoxane type 3A, covered under patent number U.S. Pat. No. 5,041,584) is combined with the first and second metal compounds to form a catalyst system.

Ionizing compounds may contain an active proton, or some other cation associated with but not coordinated to or only loosely coordinated to the remaining ion of the ionizing compound. Such compounds and the like are described in European publications EP-A-0 570 982, EP-A-0 520 732, EP-A-0 495 375, EP-A-0 426 637, EP-A-500 944, EP-A-0 277 003 and EP-A-0 277 004, and U.S. Pat. Nos. 5,153,157, 5,198,401, 5,066,741, 5,206,197, 5,241,025, 5,387,568, 5,384,299, 5,643,847 and 5,502,124, all of which are herein fully incorporated by reference. Other activators include those described in PCT publication WO 98/07515 such as tris (2, 2', 2"-nonafluorobiphenyl) fluoroaluminate, which is fully incorporated herein by reference. Combinations of activators are also contemplated by the invention, for example, alumoxanes and ionizing activators in combinations, see for example, PCT publications WO 94/07928 and WO 95/14044 and U.S. Pat. Nos. 5,153,157 and 5,453,410 all of which are herein fully incorporated by reference. Also, methods of activation such as using radiation and the like are also contemplated as activators for the purposes of this invention.

For the purposes of this patent specification and appended claims, the term "activator" is defined to be any compound or component which can activate a catalyst compounds as described above, for example, a Lewis acid or a non-coordinating ionic activator or ionizing activator or any other compound that can convert a neutral metallocene catalyst component to a metallocene cation. It is within the scope of this invention to use alumoxane or modified alumoxane as an activator, and/or to also use ionizing activators, neutral or ionic, such as tri (n-butyl) ammonium tetrakis (pentafluorophenyl) boron or a trisperfluorophenyl boron metalloid precursor which ionize the neutral metallocene compound.

There are a variety of methods for preparing alumoxane and modified alumoxanes, non-limiting examples of which are described in U.S. Pat. No. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,041,584 and 5,731,451 and European publications EP-A-0 561 476, EP-B1-0 279 586 and EP-A-0 594-218, and PCT publication WO 94/10180, all of which are herein fully incorporated by reference.

In a preferred embodiment MMAO3A, commercially available from Akzo Chemicals, Inc. under the trade name Modified Methylalumoxane type 3A and covered under patent number U.S. Pat. No. 5,041,584, is used as an activator.

The catalysts/activators/catalyst systems can be combined in situ or before being placed in the polymerization reactor. Further one metal compound can be activated and the other metal compound just added to the already activated polymerization mixture. Likewise one or more of the catalyst systems may be supported on an organic or inorganic support. Typical supports include silica, clay, talc magnesium chloride and the like. The metal compounds with or without the activator may be placed on separate supports or may be placed on the same support. Likewise the activator may be placed on the same support as the metal compound or may be placed on a separate support. The metal compounds/catalyst systems and/or their components need not be fed into the reactor in the same manner. For example, one metal compound or its components may slurried into the reactor on a support while the other metal compound or its components are provided in a solution.

In a particularly preferred embodiment [1-(2-Pyridyl)N-1-Methylethyl][1-N-2,6-Diisopropylphenyl Amido] Zirconium Tribenzyl is used in combination with tetrahydroindenyl zirconium tris pivalate and methylalumoxane.

Generally, the first and second metal catalyst compounds may be combined at molar ratios of 1:1000 to 1000:1, preferably 1:99 to 99:1, preferably 10:90 to 90:10, more preferably 20:80 to 80:20, more preferably 30:70 to 70:30, more preferably 40:60 to 60:40. The particular ratio chosen will depend on the end product desired and/or the method of activation. One practical method to determine which ratio is best to obtain the desired polymer is to start with a 1:1 ratio, measure the desired property in the product produced and adjust the ratio accordingly.

In a preferred embodiment the hydrogen concentration in the reactor is about 200–2000 ppm, preferably 250–1900 ppm, preferably 300–1800 ppm, preferably 350–1700 ppm, preferably 400–1600 ppm, preferably 500–1500 ppm, preferably 500–1400 ppm, preferably 500–1200 ppm, preferably 600–1200 ppm, preferably 700–1100 ppm, more preferably 800–1000 ppm.

In another embodiment the first metal compound is selected because when used alone it produces a high weight average molecular weight polymer (such as for example above 100,000, preferably above 150,000, preferably above 200,000, preferably above 250,000, more preferably above 300,000) and the second metal compound is selected because when used alone it produces a low molecular weight polymer (such as for example below 80,000, preferably below 70,000, preferably below 60,000, more preferably below 50,000, more preferably below 40,000, more preferably below 30,000, more preferably below 20,000 and above 5,000, more preferably below 20,000 and above 10,000).

In general the combined metal compounds and the activator are combined in ratios of about 1000:1 to about 0.5:1. In a preferred embodiment the metal compounds and the activator are combined in a ratio of about 300:1 to about 1:1, preferably about 150:1 to about 1:1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

Polymerization Process of the Invention

The catalysts and catalyst systems described above are suitable for use a solution, gas or slurry polymerization process or a combination thereof, most preferably a gas or slurry phase polymerization process.

In one embodiment, this invention is directed toward the solution, slurry or gas phase polymerization reactions involving the polymerization of one or more of monomers having from 2 to 30 carbon atoms, preferably 2–12 carbon atoms, and more preferably 2 to 8 carbon atoms. Preferred monomers include one or more of ethylene, propylene, butene-1, pentene-1, 4-methyl-pentene-1, hexene-1, octene-1, decene-1, 3-methyl-pentene-1, and cyclic olefins or a combination thereof. Other monomers can include vinyl monomers, diolefins such as dienes, polyenes, norbornene, norbornadiene monomers. Preferably a homopolymer of ethylene is produced. In another embodiment, a copolymer of ethylene and one or more of the monomers listed above is produced.

In another embodiment ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In a particularly preferred embodiment the process of the invention relates to the polymerization of ethylene and at least one comonomer having from 4 to 8 carbon atoms, preferably 4 to 7 carbon atoms. Particularly, the comonomers are butene-1, 4-methyl-pentene-1,3-methyl-pentene-1, hexene-1 and octene-1, the most preferred being hexene-1.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 75° C. to about 110° C., and most preferably in the range of from about 85° C. to about 105° C.

The productivity of the catalyst or catalyst system in a gas phase system is influenced by the main monomer partial pressure. The preferred mole percent of the main monomer, ethylene or propylene, preferably ethylene, is from about 25 to 90 mole percent and the monomer partial pressure is in the range of from about 75 psia (517 kPa) to about 300 psia (2069 kPa), which are typical conditions in a gas phase polymerization process.

In a preferred embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 185° F. (85° C.) to about 230° F. (110° C.). Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst as a slurry in isobutane or as a dry free flowing powder is injected regularly to the reactor loop, which is itself filled with circulating slurry of growing polymer particles in a diluent of isobutane containing monomer and comonomer. Hydrogen, optionally, may be added as a molecular weight control. The reactor is maintained at pressure of about 525 psig to 625 psig (3620 kPa to 4309 kPa) and at a temperature in the range of about 140° F. to about 220° F. (about 60° C. to about 104° C.) depending on the desired polymer density. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of ethylene in the reactor liquid medium is in the range of from about 1 to 10 weight percent, preferably from about 2 to about 7 weight percent, more preferably from about 2.5 to about 6 weight percent, most preferably from about 3 to about 6 weight percent.

A preferred process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. No. 5,712,352, which are herein fully incorporated by reference.

In another preferred embodiment the one or more of the supported catalysts are combined with up to 10 weight % of a metal stearate, (preferably an aluminum stearate, more preferably aluminum distearate) based upon the weight of the catalyst, any support and the stearate, preferably 2 to 6 weight %. In an alternate embodiment a solution or slurry of the metal stearate is fed into the reactor. These agents may be dry tumbled with the supported catalyst or may be fed into the reactor in a solution or slurry with or without the catalyst system or its components. In a preferred embodiment the stearate is fed into the reactor as slurry in mineral oil, preferably at about 10 weight %.

More information on using aluminum stearate type additives may be found in U.S. Ser. No. 09/113,261 filed Jul. 10, 1998, which is incorporated by reference herein.

The molecular weight of the polymer produced ( and other properties) may be changed by manipulating the polymerization system by:

1) changing the amount of the first catalyst in the polymerization system, and/or
2) changing the amount of the second catalyst in the polymerization system, and/or
3) changing the amount of hydrogen present in the polymerization process; and/or
4) changing the amount of liquid and/or gas that is withdrawn and/or purged from the process; and/or
5) changing the amount and/or composition of a recovered liquid and/or recovered gas returned to the polymerization process, said recovered liquid or recovered gas being recovered from polymer discharged from the polymerization process; and/or
6) using a hydrogenation catalyst in the polymerization process; and/or
7) changing the polymerization temperature; and/or
8) changing the ethylene partial pressure in the polymerization process; and/or
9) changing the ethylene to comonomer ratio in the polymerization process; and/or
10) changing the activator to transition metal ratio in the activation sequence, and/or 11) changing the comonomer, and/or 12) changing the catalyst activation sequence.

In a preferred embodiment, the polyolefin recovered typically has a melt index as measured by ASTM D-1238, Condition E, at 190° C. of 10 g/10 min or less, preferably 1 g/10 min or less, preferably between 0.01 and 0.5 g/10 min. In a preferred embodiment the polyolefin is ethylene homopolymer or copolymer. The comonomer is preferably a $C_3$ to $C_{20}$ linear branched or cyclic monomer, and in one embodiment is a C3 to $C_{12}$ linear or branched alpha-olefin, preferably propylene, hexene, pentene, hexene, heptene, octene, nonene, decene, dodecene, 4-methyl-pentene-1,3-methyl pentene-1,3,5,5-trimethyl hexene 1, and the like.

In a preferred embodiment the catalyst system described above is used to make a high density polyethylene having a density of between 0.930 and 0.970 g/cm$^3$ (as measured by ASTM 2839), a melt index of 0.5 or less g/10 min or less (as measured by ASTM D-1238, Condition E, at 190° C.).

The polyolefins then can be made into films, molded articles, pipes, wire and cable coating, sheets and the like. The films may be formed by any of the conventional technique known in the art including extrusion, co-extrusion, lamination, blowing and casting. The film may be obtained by the flat film or tubular process which may be followed by orientation in an uniaxial direction or in two mutually perpendicular directions in the plane of the film to the same or different extents. Particularly preferred methods to form the polymers into films include extrusion or coextrusion on a blown or cast film line.

The films produced may further contain additives such as slip, antiblock, antioxidants, pigments, fillers, antifog, UV stabilizers, antistats, polymer processing aids, neutralizers, lubricants, surfactants, pigments, dyes and nucleating agents. Preferred additives include silicon dioxide, synthetic silica, titanium dioxide, polydimethylsiloxane, calcium carbonate, metal stearates, calcium stearate, zinc stearate, talc, $BaSO_4$, diatomaceous earth, wax, carbon black, flame retarding additives, low molecular weight resins, glass beads and the like. The additives may be present in the typically effective amounts well known in the art, such as 0.001 weight % to 10 weight %.

EXAMPLES

Mn and Mw were measured by gel permeation chromatography on a waters 150° C. GPC instrument equipped with differential refraction index detectors. The GPC columns were calibrated by running a series of narrow polystyrene standards and the molecular weights were calculated using Mark Houwink coefficients for the polymer in question.

Density was measured according to ASTM D 1505.

Melt Index (MI) $I_2$ and $I_{21}$ were measured according to ASTM D-1238, Condition E, at 190° C.

Melt Index Ratio (MIR) is the ratio of $I_{21}$ over $I_2$ as determined by ASTM D-1238.

Weight % comonomer was measured by proton NMR.

MWD=Mw/Mn $I_{21}$ was measured according to ASTM D-1238, Condition E, at 190° C.

Dart Impact was measured according to ASTM D 1709.

MD and TD Tear were measured according to ASTM D 1922.

MD and TD 1% Secant modulus were measured according to ASTM D 882.

MD and TD ultimate tensile strength were measured according to ASTM D 882.

MD and TD ultimate elongation were measured according to ASTM D 412.

Haze was measured according to ASTM 1003-95, Condition A.

45° gloss was measured according to ASTM D 2457.

"PPH" is pounds per hour. "mPPH" is millipounds per hour. "ppmw" is parts per million by weight.

Catalyst A is [1-(2-Pyridyl)N-1-Methylethyl][1-N-2,6-Diisopropylphenyl Amido]Zirconium Tribenzyl and was produced as follows:

Preparation Of [1-(2-Pyridyl)N-1-Methylethyl][1-N-2,6-Diisopropylphenyl]Amine In a dry box, 22.45 mmol (6.34 g) 2-acetylpyridine(2,6-diisopropylphenylimine) were charged to a 250 mL round bottom flask equipped with a stir bar and septa. The flask was sealed, removed from the dry box and placed under nitrogen purge. Dry toluene (50 mL) was added and stirred to dissolve the ligand. The vessel was chilled to 0° C. in a wet ice bath. Trimethyl aluminum (Aldrich, 2.0 M in toluene) was added dropwise over ten minutes. The temperature of the reaction was not allowed to exceed 10° C. When addition of the trimethyl aluminum was complete, the mixture was allowed to warm slowly to room temperature, and then was then placed in an oil bath and heated to 40° C. for 25 minutes. The vessel was removed from the oil bath and placed in an ice bath. A dropping funnel containing 100 mL of 5% KOH was attached to the flask. The caustic was charged to the reaction dropwise over a 1 hour span. The mixture was transferred to a separatory funnel. The aqueous layer was removed. The solvent layer was washed with 100 mL water then 100 mL brine. The red-brown liquid product was dried over $Na_2SO_4$, vacuum stripped and placed under high vacuum over night.

80 mL of red-brown liquid was transferred to a 200 mL Schlenk flask equipped with a stir bar. A distillation head with a dry ice condenser was attached to the flask. The mixture was vacuum distilled yielding approximately 70 g of dark yellow viscous liquid product.

Preparation Of [1-(2-Pyridyl)N-1-Methylethyl][1-N-2,6-Diisopropylphenyl Amido]Zirconium Tribenzyl In a darkened room and darkened dry box, 5.0 mmol (1.45 g) of the ligand made in Example 1 were charged to a 100 mL Schlenk tube equipped with a stir bar. The ligand was dissolved in 5 mL of toluene. To a second vessel equipped with a stir bar was charged 5.5 mmol (2.5 g) tetrabenzyl zirconium and 10 mL toluene.

The ligand solution was transferred into the tetrabenzyl zirconium solution. The vessel was covered with foil and allowed to stir at room temperature in the dry box. After 6 hours at room temperature 80 mL dry hexane was added to the reaction solution and allowed to stir overnight. The reaction mixture was filtered through a medium porosity frit with approximately 2 g pale yellow solids collected.

Catalyst B (tetrahydroindenyl zirconium tris pivalate) is prepared as follows:

Synthesis of Tetrahydroindenylzirconium Trispivalate

To a solution of bis(tetrahydroindenyl)zirconium dichloride (1.182 g, 2.950 mmol) and pivalic acid (0.900 g, 8.810 mmol) in toluene (45 ml) at 25° C. was added triethylamine (0.871 g, 8.610 mmol) with stirring. A white precipitate formed immediately which was removed by filtration. The title compound was isolated as a pale-yellow powder in 75% yield by evaporating the solvent under vacuum. The title compound such prepared exhibit purity above 98% based on NMR results. $^1$H NMR (toluene-$d_8$) δ 6.24 (t, J=3.1 Hz, 1H), 5.85 (d, J=3.1 Hz, 2H), 2.72 (m, 2H), 2.48 (m, 2H), 1.91 (m, 2H), 1.49 (m, 2H), 1.14 (s, 27H). $^{13}$C NMR (toluene-$d_8$) δ 200 and 197 ($CO_2$), 114.4 and 114.1 (Cp), 39.2 ($CMe_3$), 26.48 ($CH_3$), 23.8 and 22.7 ($CH_2$).

Example 1

An ethylene hexene copolymer was produced in a 14-inch (35.6 cm) pilot plant scale gas phase reactor operating at 85° C. and 350 psig (2.4 MPa) total reactor pressure having a water cooled heat exchanger. Ethylene was fed to the reactor at a rate of about 40 pounds per hour (18 kg/hr), hexene was fed to the reactor at a rate of about 0.9 pounds per hour (0.41 kg/hr) and hydrogen was fed to the reactor at a rate of 13 mPPH. Nitrogen was fed to the reactor as a make-up gas at about 5–8 PPH. The production rate was about 21 PPH. The reactor was equipped with a plenum having about 1,600 PPH of recycle gas flow. (The plenum is a device used to create a particle lean zone in a fluidized bed gas-phase reactor. See U.S. Pat. No. 5,693,727.) A tapered catalyst injection nozzle having a 0.055 inch (0.14 cm) hole size was position in the plenum gas flow. A toluene solution containing 0.02 Moles zirconium/Liter (1:1 molar ratio of Catalyst A/Catalyst B) was contacted with 0.20 PPH of 1-hexene and MMAO-3A (1.8 wt % Aluminum in 25% heptane/75% hexane solution) in-line prior to being passing through the injection nozzle into the fluidized bed. MMAO to catalyst was controlled so that the Al:Zr molar ratio was 300:1. Nitrogen was also fed to the injection nozzle as needed to maintain a stable average particle size. A bimodal molecular weight distribution polymer having nominal 0.45 dg/min ($I_{21}$) and 0.9401 g/cc properties was obtained. The polymer was found to be approximately 70% high molecular weight (472,298) when analyzed by SEC (Size Exclusion Chromotography). Mw/Mn was 25.

Example 2

An ethylene hexene copolymer was produced in a 14-inch (35.6 cm) pilot plant scale gas phase reactor operating at 85° C. and 350 psig (2.4 MPa) total reactor pressure having a water cooled heat exchanger Ethylene was fed to the reactor at a rate of about 40 pounds per hour (18 kg/hr), hexene was fed to the reactor at a rate of about 0.6 pounds per hour (0.27 kg/hr) and hydrogen was fed to the reactor at a rate of 30 mPPH. Nitrogen was fed to the reactor as a make-up gas at about 5–8 PPH. The production rate was about 15 PPH. The reactor was equipped with a plenum having about 1,850 PPH of recycle gas flow. (The plenum is a device used to create a particle lean zone in a fluidized bed gas-phase reactor. See U.S. Pat. No. 5,693,727.) A tapered catalyst injection nozzle having a 0.055 inch (0.14 cm) hole size was position in the plenum gas flow. A toluene solution containing 0.02 Moles zirconium/Liter (0.43:1 molar ratio of Catalyst A/Catalyst B) was contacted with 0.20 PPH of 1-hexene and MMAO-3A (1 wt % Aluminum) in-line prior to being passing through the injection nozzle into the fluidized bed. MMAO to catalyst was controlled so that the Al:Zr molar ratio was 300:1. Nitrogen was also fed to the injection nozzle as needed to maintain a stable average particle size. A bimodal molecular weight distribution polymer having nominal 11.5 dg/min ($I_{21}$), 0.114 dg/min ($I_2$), 102 $I_{21}/I_2$ ratio and 0.9523 g/cc properties was obtained. The polymer was found to be approximately 50 % high molecular weight (474,200) when analyzed by SEC.

The granular resin was tumble-mixed with 1,000 ppm of Irganox 1076, 1,500 ppm of Irgafos 168, and 1,500 ppm of Calcium Stearate. They were compounded on a 2.5 inch (1 cm) single screw Prodex line at 410° F. (227° C.). The screw had one single mixing head at the end of it. The compound was evaluated on a 50 mm Alpine film extrusion line which was equipped with 100 mm die with 1 mm die gap. Both 1.0 mil (25.4 $\mu$m) and 0.5 mil (12.7 $\mu$m) film was produced with excellent film appearance rate at BUR (blow up ratio)of 4.0 with a frost line height of 36 and 40 inches (91.4 cm and 101.6 cm), respectively. Extrudability was very good with good bubble stability. The aged 0.5 mil (12.7 $\mu$m) film's dart impact strength was 210 g.

Other film mechanical properties are shown in a table below.

|  | 1 mil ((25.4 $\mu$m) | 0.5 mil ((12.7 $\mu$m) |
| --- | --- | --- |
| Mn | 9,300 | 9,300 |
| Mw | 262,940 | 262,940 |
| Mw/Mn | 28.3 | 28.3 |
| HMW/LMW | 50.4/49.6 | 50.4/49.6 |
| MI ($I_2$) dg/min | 0.114 | 0.114 |
| FI ($I_{21}$)dg/min | 11.5 | 11.5 |
| MFR ($I_{21}/I_2$) | 102 | 102 |
| Density (g/cc) | 0.9523 | 0.9523 |
| Output rate (lb/hr//kg/kr) | 104//47.2 | 104//47.2 |

-continued

|  | 1 mil ((25.4 μm) | 0.5 mil ((12.7 μm) |
|---|---|---|
| Head pressure (psi//MPa) | 7,150//493 | 7,150//493 |
| Motor Load (amp) | 57 | 57 |
| BUR | 4 | 4 |
| Frost line Height (inch) | 36 (91.4 cm) | 40(101.6 cm) |
| melt fracture | no | |
| Bubble Stability | Good | Good |
| Take-up speed (fpm//km/hr) | 92//1.7 | 184//3.4 |
| Film gauge (mil) | 1 (25.4 μm) | 0.5(12.7 μm) |
| Dart Impact strength (g) | 220 | 210 |
| Tensile str (psi//MPa) MD | 7,400//510 | 11,900//821 |
| Tensile str (psi//MPa) TD | 7,100//486 | 8,400//58 |
| Elongation (%)MD | 310 | 200 |
| Elongation (%)TD | 650 | 570 |
| Elmendorf Tear (g/mil)MD | 18(0.7 g/μm) | 15(0.6 g/μm) |
| Elmendorf Tear (g/mil)TD | 490(19 g/μm) | 230(9 g/μm) |
| Modulus (psi//MPa)MD | 119,000//8205 | 133,000//9170 |
| Modulus (psi//MPa)TD | 165,000//11376 | 182,000//12548 |

Example 3

An ethylene hexene copolymer was produced in a 14-inch (35.6 cm) pilot plant scale gas phase reactor operating at 85° C. and 350 psig (2.4 MPa) total reactor pressure having a water cooled heat exchanger Ethylene was fed to the reactor at a rate of about 42 pounds per hour (19.1 kg/hr), hexene was fed to the reactor at a rate of about 0.8 pounds per hour (0.36 kg/hr)and hydrogen was fed to the reactor at a rate of 22 mPPH. Nitrogen was fed to the reactor as a make-up gas at about 5–8 PPH. The production rate was about 19 PPH. The reactor was equipped with a plenum having about 1,300 PPH of recycle gas flow. (The plenum is a device used to create a particle lean zone in a fluidized bed gas-phase reactor. See U.S. Pat. No. 5,693,727.) A tapered catalyst injection nozzle having a 0.055 inch (0.14 cm) hole size was position in the plenum gas flow. A toluene solution containing 0.02 Moles zirconium/Liter (0.43:1 molar ratio of Catalyst A/Catalyst B) was contacted with 0.20 PPH of 1-hexene and MMAO-3A (1.8 wt % Aluminum in 25% heptane/75% hexane solution) in-line prior to being passed through the injection nozzle into the fluidized bed. MMAO to catalyst was controlled so that the Al:Zr molar ratio was 300:1. Nitrogen was also fed to the injection nozzle as needed to maintain a stable average particle size. A bimodal molecular weight distribution polymer having nominal 8.01 dg/min ($I_{21}$), 0.1 dg/min ($I_2$), 80 $I_{21}/I_2$ ratio and 0.9479 g/cc properties was obtained. The polymer was found to be approximately 56.8% high molecular weight (Mw: 448,700) when analyzed by SEC.

The granular resin was tumble-mixed with 1,000 ppm of Irganox 1076, 1,500 ppm of Irgafos 168, and 1,500 ppm of Calcium Stearate. They were compounded on a 2.5 inch (1 cm) single screw Prodex line at 410° F. (227° C.). The screw had one single mixing head at the end of it. The compound was evaluated on a 50 mm Alpine film extrusion line which was equipped with 100 mm die with 1 mm die gap. Both 1.0 mil (25.4 μm) and 0.5 mil (12.7 μm) film was produced with excellent film appearance rate at BUR (blow up ratio)of 4.0 with a frost line height of 36 and 40 inches (91.4 cm and 101.6 cm), respectively. Extrudability was very good with good bubble stability. The aged 0.5 mil (12.7 μm) film's dart impact strength was 260 g.

Other film mechanical properties are shown in a table below.

|  | 1 mil ((25.4 μm) | 0.5 mil ((12.7 μm) |
|---|---|---|
| Mn | 11,900 | 11,900 |
| Mw | 261,640 | 261,640 |
| Mw/Mn | 22 | 22 |
| HMW/LMW | 56.8/43.2 | 56.8/43.2 |
| MI ($I_2$) dg/min | 0.1 | 0.1 |
| FI ($I_{21}$)dg/min | 8.01 | 8.01 |
| MFR ($I_{21}/I_2$) | 80 | 80 |
| Density (g/cc) | 0.9479 | 0.9479 |
| Output rate (lb/hr//kg/kr) | 101//45.8 | 101//45.8 |
| Head pressure (psi//MPa) | 8220//567 | 8220//567 |
| Motor Load (amp) | 66 | 66 |
| BUR | 4 | 4 |
| Frost line Height (inch) | 36 (91.4 cm) | 40(101.6 cm) |
| melt fracture | no | |
| Bubble Stability | Fair | Fair |
| Take-up speed (fpm//km/hr) | 92//1.7 | 181//3.3 |
| Film gauge (mil) | 1 (25.4 μm) | 0.5(12.7 μm) |
| Dart Impact strength (g) | 200 | 260 |
| Tensile str (psi//MPa) MD | 9500//655 | 14000//965 |
| Tensile str (psi//MPa) TD | 7500//517 | 10800//745 |
| Elongation (%)MD | 340 | 210 |
| Elongation (%)TD | 690 | 450 |
| Elmendorf Tear (g/mil)MD | 29 | 25 |
| Elmendorf Tear (g/mil)TD | 580 | 128 |
| Modulus (psi//MPa)MD | 100,000//6895 | 99,800//6881 |
| Modulus (psi//MPa)TD | 136,200//9391 | 134,000//9239 |

Example 4

An ethylene hexene copolymer was produced in a 14-inch (35.6 cm) pilot plant scale gas phase reactor operating at 85° C. and 350 psig (2.4 MPa) total reactor pressure having a water cooled heat exchanger. Ethylene was fed to the reactor at a rate of about 48 pounds per hour (21.8 kg/hr), hexene was fed to the reactor at a rate of about 1 pound per hour (0.45 kg/hr) and hydrogen was fed to the reactor at a rate of 22 mPPH. Nitrogen was fed to the reactor as a make-up gas at about 5–8 PPH. The production rate was about 25 PPH. The reactor was equipped with a plenum having about 1,600 PPH of recycle gas flow. (The plenum is a device used to create a particle lean zone in a fluidized bed gas-phase reactor. See U.S. Pat. No. 5,693,727.) A tapered catalyst injection nozzle having a 0.055 inch (0.14 cm) hole size was position in the plenum gas flow. Two catalyst solutions were prepared in the glovebox, the first being a 0.02 Moles/Liter Catalyst A catalyst in toluene solution and the second being a 2.0 weight % solution of Catalyst B in n-hexane. The Catalyst B was contacted with a cocatalyst solution of MMAO-3A (1.8 wt % Aluminum in 25% heptane/75% hexane solution) in a continuous on-line fashion. MMAO-3A to Catalyst B was controlled so that the Al:Zr molar ratio was 300:1. A 0.20 PPH flow of 1-hexene was also present during the contacting period. The Catalyst A catalyst was likewise contacted with a cocatalyst solution of MMAO-3A (1.8 wt % Al). MMAO-3A to Catalyst A was controlled so that the Al:Zr molar ratio was 300:1. The Catalyst B catalyst solution feed was set at a specified ratio to the Catalyst A (the exact ratio is unknown because the feeders malfunctioned). The two activated catalyst solutions were mixed in-line prior to passing through the injection nozzle into the fluidized bed. Nitrogen was also fed to the injection nozzle as needed to maintain a stable average particle size. A bimodal molecular weight distribution polymer having nominal 307 dg/min ($I_{21}$), 1.4 dg/min ($I_2$), 220 $I_{21}/I_2$ ratio and 0.9531 g/cc properties was obtained.

Example 5

An ethylene hexene copolymer was produced in a 14-inch (35.6 cm) pilot plant scale gas phase reactor operating at 85°

C. and 350 psig (2.4 MPa) total reactor pressure having a water cooled heat exchanger Ethylene was fed to the reactor at a rate of about 43 pounds per hour (19.5 kg/hr), hexene was fed to the reactor at a rate of about 1.1 pound per hour (0.5 kg/hr) and hydrogen was fed to the reactor at a rate of 15 mPPH. Nitrogen was fed to the reactor as a make-up gas at about 5–8 PPH. The production rate was about 22.5 PPH. The reactor was equipped with a plenum having about 1,050 PPH of recycle gas flow. (The plenum is a device used to create a particle lean zone in a fluidized bed gas-phase reactor. See U.S. Pat. No. 5,693,727.) A tapered catalyst injection nozzle having a 0.055 inch (0.14 cm) hole size was position in the plenum gas flow. A 0.02 Moles/Liter Catalyst A catalyst in toluene solution was contacted with a cocatalyst solution of MMAO-3A (1.8 wt % Aluminum in 25% heptane/75% hexane solution) in a continuous on-line fashion. MMAO-3A to Catalyst A was controlled so that the Al:Zr molar ratio was 300:1. The activated catalyst solution was passed through the injection nozzle into the fluidized bed. Nitrogen was also fed to the injection nozzle as needed to maintain a stable average particle size. A unimodal molecular weight distribution polymer having nominal 0.23 dg/min ($I_{21}$) and 0.9298 g/cc properties was obtained.

Example 6

An ethylene hexene copolymer was produced in a 14-inch (35.6 cm) pilot plant scale gas phase reactor operating at 85° C. and 350 psig (2.4 MPa) total reactor pressure having a water cooled heat exchanger. Ethylene was fed to the reactor at a rate of about 43 pounds per hour (19.5 kg/hr), hexene was fed to the reactor at a rate of about 1.4 pound per hour (0.64 kg/hr)and hydrogen was fed to the reactor at a rate of 18 mPPH Nitrogen was fed to the reactor as a make-up gas at about 5–8 PPH. The production rate was about 23 PPH. The reactor was equipped with a plenum having about 1,600 PPH of recycle gas flow. (The plenum is a device used to create a particle lean zone in a fluidized bed gas-phase reactor. See U.S. Pat. No. 5,693,727.) A tapered catalyst injection nozzle having a 0.055 inch (0.14 cm) hole size was position in the plenum gas flow. A 2 weight % solution of Catalyst B in hexane solution was contacted with a 0.20 PPH flow of 1-hexene and a cocatalyst solution of MMAO-3A (1.0 wt % Al in hexane) in a continuous on-line fashion. MMAO-3A to Catalyst B was controlled so that the Al:Zr molar ratio was 300:1. The activated catalyst solution was passed through the injection nozzle into the fluidized bed. Nitrogen and isopentane were also fed to the injection nozzle as needed to maintain a stable average particle size. A unimodal molecular weight distribution polymer having nominal>2,000 dg/min ($I_2$) and 0.9588 g/cc properties was obtained. The $I_2$ measurement could only be estimated since the material passed through the indexer very quickly. The data are summarized in Table 1.

TABLE 1

| EXAMPLE | Catalyst(s) | $I_2$ dg/min | $I_{21}$ dg/min | $I_{21}/I_2$ | Density g/cc | % HMW by SEC |
|---|---|---|---|---|---|---|
| 1 | A/B | 0.45 | | | 0.9401 | 70 |
| 2 | A/B | 11.5 | 0.114 | 102 | 0.9489 | 50 |
| 3 | A/B | 6.2 | 007 | 89 | 0.9485 | ? |
| 4 | A/B | 307 | 1.4 | 220 | 0.9531 | ? |
| 5 | A | 0.23 | | | 0.9298 | 100 |
| 6 | B | >2,000 | | | 0.9588 | 0 |

All documents described herein are incorporated by reference herein, including any priority documents and/or testing procedures. As is apparent form the foregoing general description and the specific embodiments, while forms of the invention have been illustrated and described, various modifications can be made without departing from the spirit and scope of the invention. Accordingly it is not intended that the invention be limited thereby.

We claim:

1. A composition comprising a metallocene and a second metal compound which is represented by the formulae:

$$((Z)XA_t(YJ))_qMQ_n \quad (I)$$

or $$((R'_mZ)XA_t(YJR''_m))_qMQ_n \quad (II)$$

wherein M is a metal selected from a group consisting of the Group 3 to 13 and the lanthanide and actinide series of the Periodic Table of Elements;

Q is bonded to M and each Q is a monovalent, bivalent, or trivalent anion;

X and Y are bonded to M;

X and Y are independently carbon or a heteroatom, provided that at least one of X and Y is a heteroatom;

Y is contained in a heterocyclic ring J, wherein J comprises from 2 to 50 non-hydrogen atoms;

Z is bonded to X, wherein in formula I, Z comprises 1 to 50 non-hydrogen atoms, and in formula II, Z is a hydrocarbyl group, optionally including one or more heteroatoms;

t is 0 or 1;

when t is 1, A is a bridging group joining X and J;

q is 1 or 2;

n is the oxidation state of M minus q minus 1 if Q is a monovalent anion, n is (the oxidation state of M—q)/2, if Q is a bivalent anion or n is (the oxidation state of M—q)/3 if Q is a trivalent anion;

R" groups are bound to heterocyclic ring J and are independently selected from the group consisting of hydrogen, linear, branched or cyclic alkyl radicals, alkenyl radicals, alkynl radicals, alkoxy radicals, aryl radicals and aryloxy radicals, two or more R" groups may be joined to form a cyclic moiety, and optionally, an R" may be joined to A;

R' groups are bound to Z and are independently selected from group consisting of hydrogen, linear or branched alkyl radicals, cyclic alkyl radicals, alkenyl radicals, alkynl radicals, and aryl radicals, two or more R' groups may be joined to form a cyclic moiety, and optionally, an R' group may be joined to A; and each m is independently an integer from 0 to 5.

2. The composition of claim 1 wherein the metallocene comprises a transition metal compound represented by one of the following formulae:

wherein M is a transition metal from Group 4, 5 or 6;

L is a substituted or unsubstituted, pi-bonded ligand coordinated to M, optionally with one or more hydrocarbyl substituent groups having from 1 to 20 carbon atoms; each Q is independently selected from the group consisting of —O—, —NR—, —CR$_2$— and —S—;

Y is either C or S;

Z is selected from the group consisting of —OR, —NR$_2$, —CR$_3$, —SR, —SiR$_3$, —PR$_2$, —H, and substituted or unsubstituted aryl groups, with the proviso that when Q is —NR— then Z is selected from the group consisting of —OR, —NR$_2$, —SR, —SiR$_3$, —PR$_2$ and —H;

n is 1 or 2;

A is a univalent anionic group when n is 2 or A is a divalent anionic group when n is 1;

each R is independently a group containing carbon, silicon, nitrogen, oxygen, and/or phosphorus where one or more R groups may be attached to the L substituent;

T is a bridging group selected from the group consisting of alkylene and arylene groups containing from 1 to 10 carbon atoms optionally substituted with carbon or heteroatom(s), germanium, silicon and alkyl phosphine; and m is 2 to 7.

3. The composition of claim 1 further comprising an activator.

4. The composition of claim 1 wherein the metallocene is represented by the formula:

wherein L is a substituted or unsubstituted bulky ligand;

M is a group 4, 5 or 6 transition metal;

p is the anionic charge of L;

m is 1, 2 or 3;

A is a ligand bonded to M and capable of inserting an olefin between the M—A bond;

q is the anionic charge of A;

n is 1, 2, 3 or 4;

E is an anionic leaving group;

r is the anionic charge of E; and o is 1, 2, 3 or 4 such that (p×m)+(q×n)+(r×o) is equal to the formal oxidation state of M.

5. The composition of claim 4 wherein m is 2 and each L is independently a substituted or unsubstituted cyclopentadienyl group, substituted or unsubstituted indenyl or substituted or unsubstituted fluorenyl group.

6. The composition of claim 4, wherein m is 2 and the two L ligands are bridged together.

7. The composition of claim 4, wherein the bridge is germanium, silicon, carbon, tin, lead, nitrogen, oxygen, sulfur or phosphorus.

8. The composition of claim 1 wherein the second metal compound is represented by the formulae:

wherein R$_a$ and R$_b$ are each independently selected from the group consisting of alkyl, aryl, heterocyclic groups, and hydrogen;

R$_c$ and R$_d$ are each independently selected from the group consisting of halogens, hydrogen, alkyl, aryl, alkenyl, alkylaryl, arylalkyl, hydrocarboxy radicals having 1–20 carbon atoms, amides, phosphides, sulfides, silylalkyls, diketonates, and carboxylates; and each L is independently selected from the group consisting of halides, alkyl radicals, and arylalkyl radicals.

9. The composition of claim 8, wherein the each L is selected from the group consisting of arylalkyl radicals.

10. The composition of claim 8 wherein each L is benzyl.

11. The composition of claim 1 wherein the second metal compound is represented by the formula:

12. The composition of claim 1 wherein the activator is an alkyl aluminum compound, a non-coordinating anion, a non-coordinating group 13 metal or metalliod anion, a borane, a borate, or a mixture thereof.

13. The composition of claim 3 wherein the activator selected from the group consisting of aluminoxane, modified aluminoxane, tri (n-butyl) ammonium tetrakis (pentafluorophenyl) boron, triphenyl boron, triethyl boron, tri-n-butyl ammonium tetraethylborate, triaryl borane, and combinations thereof.

14. The composition of claim 1 wherein the metallocene comprises bis(1 methyl, 3-n-butylcyclopentadienyl) zirconium dichloride or tetrahydroindenyl zirconium tris pivalate or indenylzirconiumtrispivalate and the second metal compound is [1-(2-Pyridyl)N-1-Methylethyl][1-N-2,6-Diisopropylphenyl Amido]Zirconium Tribenzyl.

15. The composition of claim 1 wherein the metallocene and second metal catalyst compounds are combined at molar ratios of 1:1000 to 1000:1.

16. The composition of claim 3 wherein a combination of the metallocene plus the second metal compound is combined with the activator in ratios of about 1000:1 to about 0.5:1.

17. The composition of claim 3 wherein the activator is a borane, borate or aluminate and the metallocene plus the second metal compound are combined with the activator in ratios of 1:1 to about 10:1.

18. The composition of claim 1 wherein M is a group 4 metal and wherein the metallocene comprises the same metal.

* * * * *